(12) United States Patent
Filippini et al.

(10) Patent No.: US 8,703,750 B2
(45) Date of Patent: Apr. 22, 2014

(54) MIXTURES AND METHODS FOR THE INDUCTION OF RESISTANCE IN PLANTS

(75) Inventors: Lucio Filippini, Novara (IT); Marilena Gusmeroli, Monza-Milano (IT); Silvia Mormile, Novara (IT); Carlo Garavaglia, Cuggiono-Milano (IT); Luigi Mirenna, Milan (IT)

(73) Assignee: Isagro S.p.A., Milan (IT)

( * ) Notice: Subject to any disclaimer, the term of this patent is extended or adjusted under 35 U.S.C. 154(b) by 0 days.

(21) Appl. No.: 12/806,758

(22) Filed: Aug. 20, 2010

(65) Prior Publication Data

US 2010/0317519 A1     Dec. 16, 2010

Related U.S. Application Data

(62) Division of application No. 10/590,281, filed as application No. PCT/EP2005/001924 on Feb. 26, 2005, now abandoned.

(30) Foreign Application Priority Data

Mar. 2, 2004 (IT) .............................. MI2004A0402

(51) Int. Cl.
*A61K 31/60* (2006.01)
*A61K 38/06* (2006.01)
*A61K 38/07* (2006.01)
*A61K 31/715* (2006.01)

(52) U.S. Cl.
USPC .............................. 514/159; 514/21.9; 514/54

(58) Field of Classification Search
None
See application file for complete search history.

(56) References Cited

U.S. PATENT DOCUMENTS

| 4,657,928 A | 4/1987 | Sorenson |
| 5,599,529 A | 2/1997 | Cowie |

FOREIGN PATENT DOCUMENTS

| WO | WO99/33439 |   | 7/1999 |
| WO | WO00/05954 A |   | 2/2000 |
| WO | WO 03/043971 | * | 5/2003 |
| WO | WO03/043971 A |   | 5/2003 |
| WO | WO03/077654 A |   | 9/2003 |
| WO | WO03/079790 A |   | 10/2003 |

OTHER PUBLICATIONS

Matsunaga et al (FEMS Microbiol Lett 29:211-214, 1985).*
Howard (Occassional Paper Series 7(1):1-14, 2003).*
International Search Report Dated Jun. 6, 2005.
Spletzer M.E. et al. "Salicylic Acid Induces Resistance to Alternaria Solani in Hydroponically Grown Tomato", Phytopathology, St. Paul. MN (1999) pp. 722-727.
Plava T.K. et al., "Salicylic Acid Induced Resistance to Erwinia Carotovora Subsp. Carovora in Tobacco" Mmolecular Plant-Microbe Interactions, APS Press, St Paul, MN vol. 7, No. 3. (1994)pp. 356-363.
Miyachi et ., Clin.Exp Dermatol 8:305-310, (1983).

* cited by examiner

*Primary Examiner* — Craig Ricci
(74) *Attorney, Agent, or Firm* — Hedman & Costigan, P.C.; James V. Costigan; Kathleen A. Costigan

(57) ABSTRACT

Mixtures are described comprising two or more compounds selected from at least two of the following groups: i) salicylic acid and/or its functional analogous products (ESA), ii) promoting compounds (PRO) and iii) modulating compounds (MOD), and their use for stimulating the natural defense systems of plants and for inducing resistance in plants. The use is also described, of two or more compounds selected from at least two of the following groups: one or more compounds belonging to the ESA group and/or one or more compounds belonging to the PRO group and/or one or more compounds belonging to the MOD group, individually adopted by means of application programs which envisage alternating application, to stimulate the natural defense systems of plants and inducing resistance in plants.

9 Claims, No Drawings

MIXTURES AND METHODS FOR THE INDUCTION OF RESISTANCE IN PLANTS

This application is a divisional application of Ser. No. 10/590,281, filed Aug. 22, 2006 which claims the benefit of PCT/EP2005/001924 filed Feb. 26, 2005, which claims the benefit of Italian application Serial No. MI2004A000402, filed Mar. 1, 2004.

The present invention relates to mixtures and methods for inducing resistance in plants.

The induction of resistance in plants is a method for controlling diseases, which is of growing interest as it is based on the amplification of a natural process already present in plants by means of the application of products which, in themselves, can also have next to little or no bioactivity.

The natural defense process of plants comprises a complex network of messengers, regulators and genes which provide a large number of responses, said network being defined as an Innate Plant Defense (IPD) network. The functioning of this process is influenced by a number of factors which cannot always be easily controlled. Consequently, one of the problems associated with the induction of resistance in plants is the onset of undesirable effects which economically damage the crop. Large necrosed areas can in fact appear, which reduce the yield of the harvest and/or its economical value.

A possible response of the innate plant defense network does in fact envisage that the plants can synthesize biocide agents with various action mechanisms and morphologically modify the cellular structure, even as far as decreeing the death of the cell (necrosis of the vegetable tissue).

Abiotic stress factors (for example extreme temperatures, drought, salinity), which are not directly connected to phytopathogen infections, can also interfere with the IPD network.

Salicylic acid (SA) plays a key role in IPD. The starting or interruption of a specific IPD, in fact, in addition to the qualitative and quantitative modulation of its response, are an indication of the SA level in vegetable tissues. It has also been recognised that SA is both the switch of a local response and also that of a specific Systemic Acquired Resistance (SAR) which is thought to cause the expression of at least 10 pathogenesis-related proteins (PR). As each of these responses shows a different action mechanism, the induction of plant defense is considered an important means for the anti-resistance strategy (M. Lodovica Gullino, Pierre Leroux and Constance M. Smith, Crop Protection, Vol. 19 (1) (2000) pages 1-11).

The invasion of a vegetable on the part of a phytopathogen stimulates the increase in the SA content which therefore induces the self-defense of the plant against the continuation of the infection underway and allows the infection to be controlled, a control which, however, not always reaches an acceptable level. On the other hand, it is known that the addition of exogenic SA, or a functional analogous product, allows a better, and at times, total control of the oncoming infection, by stimulating preventive responses.

Single products are currently known—salicylic acid and its derivatives, acetyl salicylic acid and its derivatives, 2,6-dichloroisonicotinic acid (INA), S-methyl ester of benzo[1,2,3]thiadiazolyl-7-thiocarboxylic acid (BTH)—which, however, have a limited practical use as they are not able to exert an always reliable control of the disease.

This problem can also arise in genetically modified organisms (GMO), wherein the modification consists in maintaining an SA threshold sufficient for constantly alerting the self-defense mechanisms mediated by the same.

The use of salicylic acid or its functional analogous products, however, can cause undesired side-effects which negatively influence the quality and quantity of the treated crop. These effects are one of the causes which have not allowed a wide exploitation of resistance induction in plants in agronomical practice.

The Applicant has already previously found that salicylic acid, or its functional derivatives, have a synergetic effect with products having a direct fungicidal activity. In particular, inorganic copper compounds, known in the art and already on the market, have already been patented, which have an efficacious synergetic effect with cupric salts of derivatives of salicylic acid, as claimed in international patent application PCT/EP02/12982.

The Applicant has now surprisingly found that certain products which have a scarce or non-existent direct fungicidal activity, when in a mix with salicylic acid or its functional derivatives, are capable of amplifying the activity, also potentially increasing, however, the risk of undesired side-effects.

The Applicant has also found that the addition of specific compounds allows a surprising minimization or absence of the above undesired effects to be obtained.

The Applicant has therefore found blends and an applicative method which allow the agronomic use of IPD in an efficient and safe way, by optionally combining the components of the mixture according to the necessity of amplifying the response and/or obtaining a defense without undesired effects.

An object of the present invention consequently relates to a blend comprising two or more compounds selected from at least two of the following groups:
  i) salicylic acid and/or its functional analogous products (ESA),
  ii) promoting compounds (PRO) and
  iii) modulating compounds (MOD).

An object of the present invention is also the use of a blend comprising two or more compounds selected from two of the following groups:
  i) salicylic acid and/or its functional analogous products (ESA),
  ii) promoting compounds (PRO) and
  iii) modulating compounds (MOD),
for stimulating the natural defense systems of plants and induce resistance in the plant itself.

An object of the present invention also relates to the use of two or more compounds selected from at least two of the following groups: one or more compounds belonging to the ESA group and/or one or more compounds belonging to the PRO group and/or one or more compounds belonging to the MOD group, wherein ESA, PRO and MOD have the meanings specified above, applied singly, by means of applicative programs which envisage alternating application, to stimulate the natural defense systems of plants and to induce resistance in plants.

The use of various products for each single group allows the different physico-chemical characteristics of each product to be better exploited, so as to provide specific pharmacokinetics to better modulate its action and make the technology, object of the present invention, more efficient.

The blends thus obtained have such properties as to enable the resistance induction mechanism in plants to be exploited in agronomic practice, thus providing an extremely economically valid and reliable method also under environmental conditions which can cause abiotic stress to the plant (extreme temperatures, drought, salinity, etc. . . . ).

A further object of the present invention therefore relates to a method for stimulating the natural defense systems of plants and inducing resistance in plants, which includes the application of two or more compounds selected from at least two of the following groups: one or more compounds belonging to the ESA group and/or one or more compounds belonging to the PRO group and/or one or more compounds belonging to the MOD group, wherein ESA, PRO and MOD have the meanings specified above, both in a blend with each other or singly, by means of applicative programs which envisage their alternating application.

The method for stimulating the natural defense systems of plants, according to the present invention, is particularly advantageous as it allows the protective activity to be amplified and minimizes the phytotoxic effects associated with the above-mentioned mechanisms, called hypersensitive responses (HR) and providing a significant benefit to the vegetable, which thus remains "immunised" as a whole and more resistant to pathogen agents and various forms of abiotic stress.

In particular the promoting compounds defined PRO, when applied in a mix with salicylic acid or its functional analogous products ESA (exogenous "salicylic acid") according to the present invention, are capable of providing a synergetic effect, responsible for a surprising amplification of the biocide activity with respect to phytopathogen agents, much higher than the activity expected, as estimated by means of the Limpel formula.

ESA compounds include: salicylic acid, a derivative of salicylic acid and/or a mimetic compound of salicylic acid, or products which exert an analogous function in the plant in the induction process of systemic acquired resistance (SAR, review Ryals et al, 1996 Plant Cell vol. 8, pages 1809-1819) mediated by salicylic acid.

More specifically, the ESA compound of group i) can have the meaning of:

a salicylic compound having formula (I):

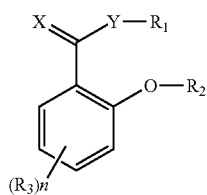

(I)

wherein:
- $R_1$ represents a hydrogen atom or a $C_1$-$C_6$ alkyl group, or a metal cation;
- $R_2$ represents a hydrogen atom or an acyl group COR', or a metal cation;
- $R_1$ and $R_2$ can jointly coordinate the same metal cation;
- R' represents a hydrogen atom or a $C_1$-$C_6$ alkyl group, or a benzyl group optionally substituted;
- $R_3$, the same or different when n is 2, represents a halogen atom, optionally selected from fluorine, chlorine, bromine and iodine, or a $C_1$-$C_6$ alkyl group, a $C_1$-$C_6$ alkoxyl group, a $C_1$-$C_6$ thioalkyl group, a $C_1$-$C_6$ thioalkoxyl group, a $C_2$-$C_7$ carbo-alkoxyl group, a cyano group, a phenyl group optionally substituted, a hydroxyl group, a nitro group;
- n is a number between 0 and 2;
- X and Y, the same or different, have the meaning of oxygen or sulphur or NH;

or ESA can mean a mimetic compound of salicylic acid having formula (IIa) or (IIb):

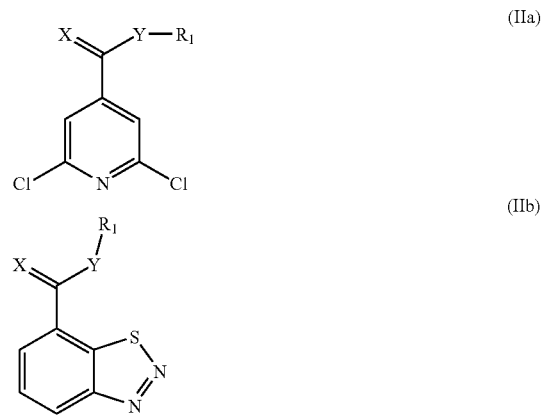

wherein $R_1$, X and Y have the meanings defined above.

Said compounds having general formula (I), (IIa) and (IIb) can also be present in hydrate form by the coordination of any number of molecules of water, and can be salified by organic bases, such as piperidine, piperazine, morpholine and natural amino acids, such as, for example, lysine, cysteine, serine.

Said compounds (I), (IIa) and (IIb), moreover, when salified with metal cations, are intended as being in any molar ratio between acid and metal, depending on the valence of the metal itself; for example, for a bivalent metal, the acid and metal ratios can be 1:1 or 1:2.

PRO compounds include products which show a scarce or null fungicidal direct activity and which can optionally induce some type of defense or, in any case, physiological perturbation of the plant.

Products defined as PRO can consequently be a wide range of products, of both a natural or synthetic origin, capable of causing such physiological perturbations to the plant as to be able to provoke situations of stress, also non-specific. All resistance inductors can therefore be included, which are known for not being functional analogous products of SA, the same non-virulent or virulent microorganisms, when used in sub-lethal dosages, part of the same which can induce recognition of the pathogen, substances capable of exciting biological systems of the plant causing stress and/or defense responses, also non-specific, and also the use of non-selective chemicals for the plant itself (even herbicides) in sub-lethal dosages.

More specifically, the PRO compound of group ii), subdivided into the sub-groups a-f, can have the following meanings:

a: salts or oxides of metals such as sodium, lithium, potassium, magnesium, calcium, copper, zinc, iron, manganese, as sulphates, nitrates, phosphates, phosphonates or phosphites, carbonates or organic chelates, such as, for example, titanium dioxide, titanium citrate, titanium malate, zinc oxide, zinc sulphate, zinc nitrate, iron sulphate, iron nitrate, calcium sulphate, iron oxides, magnesium sulphate, copper sulphate, zinc carbonate, calcium phosphate, silica, silicic acid, iron polycarboxylates;

b: dyes and pigments, such as, for example, Prussian blue, Bengal pink, phthalocyanines, metal porphyrins, natural or synthesis optical bluing products, such as, for example, esculetin, esculin, umbellipheron, stilbenic derivatives;

c: saccharides and derivatives, such as, for example, glucosamine, chitin, chitosane, glucanes, such as, for example, lamarine or glucopyranes optionally substituted with fatty acids or galactomannans, such as, for example, guar;

d: nitroso donor compounds, such as, for example, sodium nitroferrocyanide;

e: organic acids and derivatives such as esters and amides, for example, aspartame and saccharin; amino acids such as for example benzoic acid, cinnamic acid, propionic acid, 1-amino-1-cyclopropancarboxylic acid, β-aminobutyric acid (BABA), free dextrorotatory amino acids of the protein type, or incorporated in oligopeptides, or blends of said dextro- or levorotatory free amino acids or incorporated in oligopeptides;

f: proteins inducing immune vegetable responses such as arpine.

MOD compounds include products capable of reducing/eliminating the necrotized surfaces caused by agents involved in hypersensitive responses (HR), or by agents in any case toxic, amplified in their action by SA, possibly strengthened by stress conditions, improving the activity of the phytoiatric mixture and widening its application on site.

As a result of these specific characteristics, MOD compounds can be applied in a blend or alternated with other components of the method object of the present invention, with the first appearance, or preferably for precautionary measures, of symptoms of hypersensitive responses, also on genetically modified plants.

More specifically, the MOD compound of group iii) can have the meaning of:

glutathione (GSH), or a compound capable of favouring accumulation in vegetable tissues, 4-hydroxyproline and its derivatives, allantoine, L-glutamic acid and its derivatives, tert-butylhydroquinone, betaine, cystine, cysteine, or its derivative having formula (III):

(III)

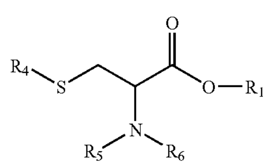

wherein:

$R_1$ has the meanings defined above, $R_4$ and $R_5$, the same or different, can have the meaning of a hydrogen atom, a $C_1$-$C_6$ alkyl group, a methyl carboxylic group, a $C_2$-$C_7$ methyl carboalkoxylic group, an optionally substituted phenyl group, $R_4$ and $R_5$, jointly, can have the meaning of the alkylidene group $-(CH_2)_m-$, m has the value of 1 or 2, $R_6$ represents a hydrogen atom, or an acyl COR' group.

Said compounds having general formula (III) can also be present in hydrate form, by the coordination of any number of molecules of water, and can be salified by organic bases, such as piperidine, piperazine, morpholine and natural amino acids, such as, for example, lysine.

In particular, the blend comprising one or more MOD compounds, applied together with one or more PRO compounds, in the presence or absence of one or more ESA compounds, exerts these beneficial effects, capable of minimising or avoiding undesired side-effects.

The application of one or more MOD compound together with β-aminobutyric acid (BABA), for example, known for limiting leaf diseases but generating necrosis (Physiological and Molecular Plant Pathology (1994), vol. 44, pages 273-288), produces a reduction in or the elimination of the effect.

In the previously mentioned formulae, $C_1$-$C_6$ alkyl group means a linear or branched $C_1$-$C_6$ alkyl group, possibly substituted, the substituents being the same or different.

Examples of this group are: methyl, ethyl, propyl, isopropyl, tert-butyl, amyl, hexyl.

$C_1$-$C_6$ alkoxyl group means a $C_1$-$C_6$ alkoxyl group in which the aliphatic portion is a $C_1$-$C_6$ alkyl group, as previously defined.

Examples of this group are: methoxyl, ethoxyl, butoxyl.

$C_1$-$C_6$ thioalkyl group means a $C_1$-$C_6$ thioalkyl group in which the aliphatic portion is a $C_1$-$C_6$ alkyl group, as previously defined. Examples of this group are: thiomethyl, thioethyl, thioamyl.

$C_1$-$C_6$ thio-alkoxyl group means a $C_1$-$C_6$ thioalkoxyl group in which the aliphatic portion is a $C_1$-$C_6$ alkyl group, as previously defined. Examples of this group are: thiomethoxyl, thioethoxyl, thiopropoxyl.

$C_2$-$C_7$ carboalkoxyl group means a $C_2$-$C_7$ carboalkoxyl group in which the aliphatic portion is a $C_1$-$C_6$ alkyl group, as previously defined.

Examples of this group are: carboxymethyl, carboxyethyl, carboxypropyl, carboxyhexyl.

Metal cation means a metal cation that can be mono-, di-, tri- or tetra-valent.

Examples of metals are: sodium, lithium, potassium, magnesium, calcium, copper, zinc, iron, manganese.

In the previous definitions, optionally substituted refers to one or more substituents, the same or different, selected from the following groups: halogen atoms, alkyl, alkoxyl, alkylthio, cyano, hydroxy, amino-carbonyl, carboalkoxyl.

Examples of preferred ESA compounds are the following:

salicylic acid,
copper (II) salt of salicylic acid,
zinc (II) salt of salicylic acid,
calcium (II) salt of salicylic acid,
magnesium (II) salt of salicylic acid,
iron (II) salt of salicylic acid,
iron (III) salt of salicylic acid,
manganese (II) salt of salicylic acid,
sodium salt of salicylic acid,
potassium salt of salicylic acid,
methyl ester of salicylic acid,
ethyl ester of salicylic acid,
isopropyl ester of salicylic acid,
methyl thioester of salicylic acid,
methyl thioester of thiosalicylic acid,
ethyl thioester of salicylic acid,
ethyl thioester of thiosalicylic acid,
acetylsalicylic acid,
copper (II) salt of acetylsalicylic acid,
zinc (II) salt of acetylsalicylic acid,
calcium (II) salt of acetylsalicylic acid,
magnesium (II) salt of acetylsalicylic acid,
iron (II) salt of acetylsalicylic acid,
iron (III) salt of acetylsalicylic acid,
manganese (II) salt of acetylsalicylic acid,
sodium salt of acetylsalicylic acid,
potassium salt of acetylsalicylic acid,
methyl ester of acetylsalicylic acid,
ethyl ester of acetylsalicylic acid,
isopropyl ester of acetylsalicylic acid,
methyl thioester of acetylsalicylic acid,
methyl thioester of acetylthiosalicylic acid
ethyl thioester of acetylsalicylic acid
ethyl thioester of acetylthiosalicylic acid 5-chlorosalicylic acid
copper (II) salt of 5-chlorosalicylic acid,
zinc (II) salt of 5-chlorosalicylic acid,
calcium (II) salt of 5-chlorosalicylic acid,
magnesium (II) salt of 5-chlorosalicylic acid,
iron (II) salt of 5-chlorosalicylic acid,
iron (III) salt of 5-chlorosalicylic acid,
manganese (II) salt of 5-chlorosalicylic acid,
sodium salt of 5-chlorosalicylic acid,
potassium salt of 5-chlorosalicylic acid,
methyl ester of 5-chlorosalicylic acid,
ethyl ester of 5-chlorosalicylic acid,
isopropyl ester of 5-chlorosalicylic acid,
5-chloroacetylsalicylic acid,
copper (II) salt of 5-chloroacetylsalicylic acid,
zinc (II) salt of 5-chloroacetylsalicylic acid,
calcium (II) salt of 5-chloroacetylsalicylic acid,
magnesium (II) salt of 5-chloroacetylsalicylic acid
iron (II) salt of 5-chloroacetylsalicylic acid,
iron (III) salt of 5-chloroacetylsalicylic acid,
manganese (II) salt of 5-chloroacetylsalicylic acid
sodium salt of 5-chloroacetylsalicylic acid,
potassium salt of 5-chloroacetylsalicylic acid,
methyl ester of 5-chloroacetylsalicylic acid,
ethyl ester of 5-chloroacetylsalicylic acid,
isopropyl ester of 5-chloroacetylsalicylic acid,
2,6-dihydroxybenzoic acid,
copper (II) salt of 2,6-dihydroxybenzoic acid,
methyl ester of 2,6-dihydroxybenzoic acid,
iron (II) salt of 2,6-dihydroxybenzoic acid,
3-methylsalicylic acid,
3-methylacetylsalicylic acid,
3-methoxysalicylic acid,
3-methoxyacetylsalicylic acid,
3-thiomethylsalicycilc acid,
3-thiomethylacetylsalicylic acid,
3-thiomethoxysalicylic acid,
3-thiomethoxyacetylsalicylic acid,
3-phenylsalicylic acid,
3-phenylacetylsalicylic acid,
copper (II) salt of 3-phenylsalicylic acid,
copper (II) salt of 3-phenylacetylsalicylic acid,
3-methoxycarbonylsalicylic acid,
3-methoxycarbonylacetylsalicylic acid,
3-cyanosalicylic acid,
3-cyanoacetylsalicylic acid,
copper (II) salt of 3-methoxysalicylic acid,
copper (II) salt of 3-methoxyacetylsalicylic acid,
5-nitrosalicylic acid,
5-nitroacetylsalicylic acid,
copper (II) salt of 5-nitrosalicylic acid,
copper (II) salt of 5-nitroacetylsalicylic acid,
sodium salt of 5-nitrosalicylic acid,
sodium salt of 5-nitroacetylsalicylic acid,
iron (II) salt of 5-nitrosalicylic acid,
iron (II) salt of 5-nitroacetylsalicylic acid,
zinc (II) salt of 5-nitrosalicylic acid,
zinc (II) salt of 5-nitroacetylsalicylic acid,
2,6-dichloroisonicotinic acid,
methyl ester of 2,6-dichloroisonicotinic acid,
ethyl ester of 2,6-dichloroisonicotinic acid,
thiomethyl ester of 2,6-dichloroisonicotinic thioacid,
copper (II) salt of 2,6-dichloroisonicotinic acid,
iron (II) salt of 2,6-dichloroisonicotinic acid,
iron (III) salt of 2,6-dichloroisonicotinic acid,
zinc (II) salt of 2,6-dichloroisonicotinic acid,
magnesium (II) salt of 2,6-dichloroisonicotinic acid,
sodium salt of 2,6-dichloroisonicotinic acid,
potassium salt of 2,6-dichloroisonicotinic acid,
S-methylester of benzo[1,2,3]thiadiazolyl-7-thiocarboxylic acid,
methyl ester of benzo[1,2,3]thiadiazolyl-7-thiocarboxylic acid,
methyl ester of benzo[1,2,3]thiadiazolyl-7-carboxylic acid,
benzo[1,2,3]thiadiazolyl-7-thiocarboxylic acid,
benzo[1,2,3]thiadiazolyl-7-carboxylic acid,
copper (II) salt of benzo[1,2,3]thiadiazolyl-7-thiocarboxylic acid,
magnesium (II) salt of benzo[1,2,3]thiadiazolyl-7-thiocarboxylic acid,
zinc (II) salt of benzo[1,2,3]thiadiazolyl-7-thiocarboxylic acid,
sodium salt of benzo[1,2,3]thiadiazolyl-7-thiocarboxylic acid,
potassium salt of benzo[1,2,3]thiadiazolyl-7-thiocarboxylic acid,
iron (II) salt of benzo[1,2,3]thiadiazolyl-7-thiocarboxylic acid,
iron (III) salt of benzo[1,2,3]thiadiazolyl-7-thiocarboxylic acid, Salts of bivalent metals are salts in which the molar ratios acid:metal can be 1:1 or 2:1, for example $Cu^{2+}SA_2$, $Cu^{2+}SA$.

Examples of PRO compounds are the following:
titanium dioxide,
zinc oxide,
iron oxides,
copper oxide,
iron nitrate,
zinc nitrate,
calcium nitrate,
magnesium nitrate,
copper nitrate,
copper sulphate,
zinc sulphate,
iron sulphate,
calcium sulphate,
magnesium sulphate,
silica,
silicic acid,
calcium phosphate,
zinc phosphate,
magnesium phosphate,
mono-potassium salt of phosphorous acid,
di-potassium salt of phosphorous acid,
50:50 blends of mono-potassium salt of phosphorous acid and di-potassium salt of phosphorous acid,
copper carbonate,
zinc carbonate,
Prussian blue,
sodium nitroferrocyanide (III),
glucosamine,
N-acetylglucosamine,
glucosamine pentaacetate,
chitin,
chitosane,
benzoic acid,
3-chlorobenzoic acid,
4-chlorobenzoic acid,
3-bromobenzoic acid,
4-bromobenzoic acid,
3-methylbenzoic acid,
3,4-dimethoxybenzoic acid,
3,4-dihydroxybenzoic acid, vanillic acid
cinnamic acid,
β-aminobutyric acid (BABA),
γ-aminobutyric acid (GABA),
guar,
arpine,
commercial protein hydrolyzed products of an animal origin,
commercial protein hydrolyzed products of a vegetable origin,
titanium citrate,
titanium malate,
Bengal pink,
copper phthalocyanine,
iron phthalocyanine,
zinc phthalocyanine,
magnesium phthalocyanine,
copper chlorophthalocyanines,
copper sulfophthalocyanines,
metal porphirins,
chlorophyll,
esculetin,
esculin,
umbellipheron,
C.I. 40650,
C.I. 40676,
glucopiranosyl pentastearate,
glucopiranosyl pentalaurate,
laminarin,
aspartame
saccharin,
iron chelated saccharide polyacrylic copolymer (Beixon AB).

Examples of MOD compounds are the following:
glutathione,
Benoxacor,
Dichlormid,
Furilazol,
MG 191,
Dicyclonon,
4-thiazolidinecarboxylic acid (TCA),
N-acetyl-4-thiazolidinecarboxyic acid (ATCA),
N-benzoil-4-thiazolidinecarboxylic acid,
N-formyl-4-thiazolidinecarboxylic acid,
sodium salt of N-acetyl-4-thiazolidinecarboxylic acid,
copper (II) salt of N-acetyl-4-thiazolidine-carboxylic acid,
iron (II) salt of N-acetyl-4-thiazolidine-carboxylic acid,
sodium salt of 4-thiazolidinecarboxylic acid,
copper (II) salt of 4-thiazolidinecarboxylic acid,
iron (II) salt of 4-thiazolidinecarboxylic acid,
methyl ester of 4-thiazolidinecarboxylic acid,
methyl ester of N-acetyl-4-thiazolidinecarboxylic acid,
ethyl ester of 4-thiazolidinecarboxylic acid,
ethyl ester of N-acetyl-4-thiazolidinecarboxylic acid,
isopropyl ester of 4-thiazolidinecarboxylic acid,
isopropyl ester of N-acetyl-4-thiazolidinecarboxylic acid,
4-hydroxyproline,
copper salt of 4-hydroxyproline,
methyl ester of 4-hydroxyproline,
sodium salt of 4-hydroxyproline,
N-acetyl-4-hydroxyproline,
N,O-diacetyl-4-hydroxyproline,
allantoine,
allantoic acid,
L-glutamic acid,
ethyl diester of glutamic acid,
methyl diester of glutamic acid,
N-acetyl glutamic acid,
monosodium salt of L-glutamic acid,
disodium salt of L-glutamic acid,
copper (II) salt of L-glutamic acid,
iron (II) salt of L-glutamic acid,
zinc (II) salt of L-glutamic acid,
tert-butylhydroquinone,
cysteine,
N-acetylcysteine,
N-benzoylcysteine,
methyl ester of S-carboxymethylcysteine,
S-carboxymethylcysteine,
S-carboxymethylcysteine lysine salt,
S-methoxycarbonylmethylcysteine,
methyl ester of S-methoxycarbonylmethylcysteine,
cystine,
N,N-diacetylcystine,
methyl diester of cystine,
betaine.

The compounds indicated as PRO, in particular the PRO compounds pertaining to the sub-group a), (for example titanium dioxide, zinc oxide, silicic acid) are preferably in micronized form with a particle size lower than 1 micron.

An important advantage of the method for stimulating the natural defense systems of plants according to the present invention, consists in allowing the induction of the natural defenses the plant for agronomical purposes, so that the magnitude of the response can be modulated and the response can be reliable with respect to the possible appearance of side-effects which can jeopardize the quality and quantity of the crops treated.

This method therefore envisages applicative programs which involve the application of one or more compounds, among which salicylic acid and its functional homologous products already defined as ESA, blended or alternating with one or more compounds, already defined as PRO, capable of amplifying the response induced by ESA, and/or in a blend or alternating with one or more compounds already defined as MOD, capable of minimizing and/or eliminating undesired side-effects which can cause qualitative or quantitative damage to the crops treated.

The use of blends of one or more PRO compounds, responsible for occasional necrosis when applied to crops under critical biotic and abiotic conditions, is therefore within the spirit of the present invention, in blends or alternated with ESA compounds.

Again within the spirit of the present invention is the use of blends of one or more PRO compounds, responsible for occasional necrosis when applied to crops under critical biotic and abiotic conditions, in blends or alternated with MOD compounds.

Yet again within the spirit of the present invention is the use of blends of one or more ESA compounds, known for inducing SAR, in blends or alternated with MOD compounds.

As mentioned above, an object of the present invention relates to a method for stimulating the natural defense systems of plants and inducing resistance in the plant, which includes the application of two or more compounds selected from at least two of the following groups: one or more compounds belonging to the ESA group and/or one or more compounds belonging to the PRO group and/or one or more compounds belonging to the MOD group, wherein ESA, PRO and MOD have the above-mentioned meanings, either mixed with each other or individually, through applicative programs which envisage their alternating use.

Examples of preferred blends are:
salicylic acid+titanium dioxide+TCA,
acetylsalicylic acid+Prussian blue+ATCA,
salicylic acid+Prussian blue+ATCA,
copper (II) salt of salicylic acid+iron sulphate,
copper (II) salt of 5-chloroacetylsalicylic acid+iron sulphate+glutathione,
copper (II) salt of acetylsalicylic acid+titanium dioxide,
copper (II) salt of acetylsalicylic acid+titanium dioxide+Prussian blue,
copper (II) salt of acetylsalicylic acid+iron sulphate,
copper (II) salt of acetylsalicylic acid+zinc sulphate,
copper (II) salt of acetylsalicylic acid+copper sulphate,
copper (II) salt of acetylsalicylic acid+zinc oxide,
copper (II) salt of acetylsalicylic acid+copper phthalocyanine,
2,6-dichloroisonicotinic acid (INA)+ATCA,
S-methyl ester of benzo[1,2,3]thiadiazolyl-7-thiocarboxilic acid (ETH)+ATCA+TCA,
BABA+ATCA+TCA,
BABA+cysteine,
copper (II) salt of salicylic acid+chitosane+glutamic acid,
copper (II) salt of acetylsalicylic acid+chitosane+glutathione,
copper (II) salt of acetylsalicylic acid+terbutylhydroquinone,
salicylic acid+iron sulphate,
salicylic acid+zinc sulphate,
copper (II) salt of salicylic acid+iron sulphate,
copper (II) salt of salicylic acid+zinc sulphate,
copper (II) salt of acetylsalicylic acid+iron phthalocyanine,
copper (II) salt of acetylsalicylic acid+zinc phthalocyanine,
copper (II) salt of acetylsalicylic acid+cysteine+iron (II) salt of glutamic acid,
copper (II) salt of acetylsalicylic acid+glucosamine+ATCA,
copper (II) salt of acetylsalicylic acid+titanium citrate,
copper (II) salt of acetylsalicylic acid+titanium malate,
copper (II) salt of acetylsalicylic acid+copper carbonate,
copper (II) salt of acetylsalicylic acid+copper carbonate+acetylcysteine,
copper (II) salt of acetylsalicylic acid+calcium phosphate+terbutylhydroquinone.

The compounds called ESA, PRO and MOD are products on the market or which can be obtained through the most common synthesis methods known in literature.

The method for stimulating the natural defense systems of plants according of the present invention, allows many fungi n and bacterial phytopathogens or viruses to be controlled.

More specifically, the blends according to the present invention have a particularly high fungicidal activity against phytopathogen fungi which attack crops of vines, tobacco, sugar beet, cereals, vegetables, rice, Cucurbitaceae, fruit trees.

Examples of phytopathogen fungi which can be efficaciously fought by means of this technology, are:
*Erysiphe* spp. on cereals;
*Puccinia* spp. on cereals;
*Plasmopara viticola* on vines;
*Pythium* spp. on vegetables;
*Phytophthora* spp. on vegetables;
*Peronospera tabacina* on tobacco;
*Septoria* spp. on cereals;
*Sphaerotheca fuliginea* on Cucurbitaceae (for example cucumber);
*Pseudoperonospera cubensis* on cucurbitaceae;
*Pyricularia oryzae* on rice;
*Uncinula necator* on vines;
*Venturia* spp. on fruit trees;
*Botrytis cinerea* on vines and vegetables;
*Fusarium* spp. on cereals;
*Alternaria* spp. on fruit trees and vegetables;
*Bremia* on salads and spinach.

This method for stimulating the natural defense systems of plants and inducing resistance in plants, according to the present invention, is capable of exerting a fungicidal action of both a curative and preventive nature.

A further object of the present invention relates to a method for controlling phytopathogen fungi in agricultural crops, which includes the use of two or more compounds selected from at least two of the following groups: one or more compounds belonging to the ESA group and/or one or more compounds belonging to the PRO group and/or one or more compounds belonging to the MOD group, wherein ESA, PRO and MOD have the above-mentioned meanings, both in blends and through applicative programs which envisage their alternated use.

The amount of each compound, selected from those defined as ESA, PRO and MOD, to be applied for obtaining the desired effect can vary according to several factors, such as, for example, the compound used, the crop to be preserved, the type of pathogen, the degree of infection, the climatic conditions, the application method, the formulation adopted.

The dosage of each compound selected from ESA, PRO and MOD, can range from 0.5 g to 5 kg per hectare and normally provide a sufficient control.

The application of this method can be effected on all parts of the plant, for example on the leaves, stems, branches and roots, or on the seed itself before sowing, or on the ground in which the plant grows.

Blends formulated in the form of dry powders, wettable powders, emulsifying concentrates, micro-emulsions, pastes, granulates, solutions, suspensions, etc. . . . can be adopted: the choice of the type of formulation will depend on the specific use.

The blends are prepared in the known way, for example by diluting or dissolving the active substance with a solvent medium and/or a solid diluent, possibly in the presence of surfactants.

Solid diluents or supports which can be used, are for example: silica, kaolin, bentonite, talc, infusorial earth, dolomite, calcium carbonate, magnesia, gypsum, clay, synthetic silicates, attapulgite, sepiolite.

Liquid diluents which can be used, are for example, in addition to water, aromatic organic solvents (xylols or blends of alkylbenzols, chlorobenzenes, etc. . . . ) paraffins (petroleum fractions), alcohols (methanol, propanol, butanol, octanol, glycerine, etc. . . . ), esters (ethyl or isobutyl acetate, etc. . . . ) ketones (cyclohexanone, acetone, acetophenone, isophorone, ethyl amyl ketone, etc. . . . ), amides (N,N-dimethylformamide, N-methylpirrolydone, etc. . . . ).

Sodium salts, calcium salts, triethylamine or triethanolamine, alkylaryl sulphonates, polyethoxylated alkylphenols, polyethoxylated esters of sorbitol, ligninsulphonates, etc. . . . can be used as surfactants.

The blends according to the present invention can also contain special additives for particular purposes, for example adhesive agents, such as gum Arabic, polyvinylalcohol, polyvinylpyrrolidone, etc. . . . .

When desired, other compatible active principles can be added to the blend according to the present invention, such as, for example, other fungicides, phytoregulators, antibiotics, herbicides, insecticides, fertilizers.

Preferably, the products already claimed in international patent application PTC/EP02/12982 can be used.

Examples of other fungicides which can be included in the compositions of the invention are: AC-382042, ampropylfos, anilazine, azaconazole, azoxystrobin, benalaxyl (in its racemic form or as an optically active R isomer), benclothiaz, benomyl, bitertanol, blasticidin-S, bromuconazole, bupirimate, buthiobate, captafol, captan, carbendazim, carboxin, carpropamid, chinomethionat, chloroneb, chlorothalonil, chlozolinate, cyazofamid, cymoxanil, cyproconazole, cyprodinil, debacarb, dichlofluanid, dichlone, diclobutrazol, diclomezine, dicloran, dicyclomet, diethofencarb, diphenoconazole, diflumetorim, dimethirimol, dimethomorph, diniconazole, dinocap, dipyrithione, ditalimfos, dithianon, dodemorph, dodine, edifenphos, epoxyconazole, etaconazole, ethaboxam, ethirimol, ethoxyquin, etridiazole, famoxadone, fenamidone, fenaminosulf, fenapanyl, fenarimol, fenbuconazole, fenfuram, fenhexamid, fenpiclonyl, fenpropidin, fenpropimorph, fentin, ferbam, ferimzone, fluazinam, fludioxonyl, flumetover, flumorph, fluoroimide, fluotrimazole, fluoxastrobin, fluquinconazole, flusilazole, flusulfamide, flutolanil, flutriafol, folpet, fosetylaluminium, fuberidazole, furalaxyl, furconazole, guazatine, hexaconazole, hydroxyquinoline sulfate, hymexazol, ICIA0858, imazalil, imibenconazole, iminoctadine, ipconazole, iprobenfos, iprodione, IR5885, isoprothiolane, iprovalicarb, kasugamycin, kresoxim-methyl, mancopper, mancozeb, maneb, mebenil, mepanipyrim, mepronil, metalaxyl, metalaxyl-M, metconazole, methfuroxam, metiram, metsulfovax, MON-65500, myclobutanil, natamycin, nitrothal-isopropyl, nuarimol, ofurace, orisastrobin, oxadixyl, oxycarboxin, pefurazoate, penconazole, pencycuron, pentachlorophenol and its salats, phthalide, piperalin, Bordeaux mixture, polyoxins, probenazole, prochloraz, procymidone, propamocarb, propiconazole, propineb, proquinazid, prothiocarb, prothioconazole, pycoxystrobin, pyracarbolid, pyraclostrobin, pyrazophos, pyrifenox, pyrimethanil, pyroquilon, pyroxyfur, quinacetol, quinazamid, quinconazole, quinoxyfen, quintozene, rabenazole, cuprum hydroxyde, cuprum oxychloride, cuprum sulfate, RH-7281, RPA-407213, simeconazole, spiroxamine, spiromesifen, metominostrobin, streptomycin, SYP-L-190, tebuconazole, tetraconazole, thiabendazole, thicyofen, thifluzamide, thiophanate-methyl, thiram, tioxymid, tolclofos-methyl, tolylfluanid, triadimefon, triadimenol, triarimol, triazbutil, triazoxide, tricyclazole, tridemorf, trifloxystrobin (CGA 279202), triflumizole, triforine, triticonazole, validamycin, vinclozolin, zineb, ziram, sulphur, zoxamide.

These fungicidal compounds are products already on the market or about to be commercialized. Their description can be easily found in technical literature, for example in "The pesticide manual", 2000, XII edition, British Crop Protection Council Ed.

IR5885 refers to one of the compounds among those claimed in patent application EP-A-1028125.

The concentration of active principle in the above blends can vary within a wide range depending on the active compound, the applications for which it is destined, the environmental conditions and type of formulation adopted.

The concentration of active principle generally ranges from 1 to 90%, preferably from 5 to 50%.

The following examples for the application of the method according to the present invention are provided for illustrative but non-limiting purposes of the present invention.

EXAMPLE 1

Efficacy of Blends of One or More Compounds Belonging to the Groups of Compounds ESA, PRO and MOD in the Control of *Plasmopara viticola* on Vines in Preventive Leaf Application (Greenhouse Test)

Table 1-Table 4

Leaves of cultivar Merlot vines, grown in vases, in a conditioned environment (20±1° C., 70% relative humidity), were treated by spraying both sides of the leaves with the blends in question dispersed in an aqueous solution containing 0.3% of tween 20.

After remaining 7 days in a conditioned environment, the plants were infected on the lower side with an aqueous suspension of *Plasmorpara viticola* spores (200,000 spores per $cm^3$).

The plants were kept in a humidity saturated environment, at 21° C., for the incubation period of the fungus and, at the end of this period (7 days), the fungicidal activity is evaluated according to an evaluation percentage scale from 100 (healthy plant) to 0 (completely infected plant).

From the data indicated in Table 1 and 2, it is possible to verify the synergetic effect of the blends, consisting of the blends being tested, compared with the expected efficacy using the Limpel formula ("Pesticide Science" (1987), vol. 19, pages 309-315):

$$E = x + y - (xy/100)$$

wherein:

E is the expected fungicidal activity, in the absence of synergetic effects, from a blend obtained by mixing g.x of the compound X with g.y of the compound Y;

x is the activity of compound X when used alone at a dose of g.x;

y is the activity of compound Y when used alone at a dose of g.y.

When the fungicidal activity found experimentally is greater than the value of E, said activity should be considered as being a synergetic effect.

TABLE 1

7-day preventive activity on *Plasmopara viticola* of blends of the copper (II) salt of acetylsalicylic acid ($Cu^{2+}$ $ASA_2$), which at 64 ppm*(g · x) is 78 (x).

| Blends | Doses ppm* (g · y) | Activity (y) | Blend activity according to Limpel (E) | Experimental blend activity | Synergy Factor | Undesired effects |
|---|---|---|---|---|---|---|
| **$TiO_2$ | 24 | 24 | 83.28 | 100 | 1.20 | 0 |
| Prussian blue | 12.5 | 13 | 80.86 | 100 | 1.24 | 0 |

TABLE 1-continued 7-day preventive activity on *Plasmopara viticola* of blends of the copper (II) salt of acetylsalicylic acid ($Cu^{2+}$ $ASA_2$), which at 64 ppm*(g · x) is 78 (x).

| Blends | Doses ppm* (g · y) | Activity (y) | Blend activity according to Limpel (E) | Experimental blend activity | Synergy Factor | Undesired effects |
|---|---|---|---|---|---|---|
| $FeSO_4$ | 28 | 40 | 86.80 | 100 | 1.15 | 0 |
| $ZnSO_4$ | 33 | 22 | 82.84 | 100 | 1.21 | 0 |
| $CuSO_4$ | 32 | 48 | 88.56 | 100 | 1.13 | 0 |
| **ZnO | 33 | 30 | 84.60 | 99 | 1.17 | 0 |
| Saccharide polyacrilyc co-polymer (Beixon AB) | 28 | 7 | 79.54 | 90 | 1.13 | 0 |

*the doses in ppm refer to the quantity of Equivalent Metal;
**$TiO_2$ has a particle size equal to 0.15 micron; ZnO has a particle size ranging of from 0.05 to 0.07 micron.

Undesired effects refer to the appearance of necrosis or leaf decolouring.

TABLE 2

7-day preventive activity on *Plasmopara viticola* of blends of the copper (II) salt of acetylsalicylic acid ($Cu^{2+}$ $ASA_2$), which at 50 ppm*(g · x) is 66 (x).

| Blends | Doses ppm* (g · y) | Activity (y) | Blend activity according to Limpel (E) | Experimental blend activity | Synergy Factor | Undesired Effects |
|---|---|---|---|---|---|---|
| Fe (II) phthalocyanine | *28 | 14 | 70.76 | 95 | 1.34 | 0 |
| Cu (II) Phthalocyanine | *32 | 10 | 69.4 | 80 | 1.15 | 0 |
| $FeNH_4SO_4$ | *28 | 18 | 72.12 | 93 | 1.29 | 0 |
| Tetracopper oxychloride | *50 | 28 | 75.52 | 98 | 1.29 | 0 |
| Cu oxychloride | *50 | 18 | 72.12 | 93 | 1.29 | 0 |
| Cu hydroxide | *50 | 34 | 77.56 | 97 | 1.25 | 0 |
| Fe (II) gluconate | *28 | 28 | 75.52 | 92 | 1.22 | 0 |
| Silicic acid | *14 | 14 | 70.76 | 96 | 1.36 | 0 |
| Sodium nitroironcyanide | *50 | 38 | 78.92 | 98 | 1.24 | 0 |
| Fe(III) glutamate | *28 | 16 | 71.44 | 93 | 1.30 | 0 |
| Esculine | ♦25 | 10 | 69.40 | 86 | 1.24 | 0 |
| Cumarine | ♦25 | 10 | 69.40 | 90 | 1.30 | 0 |
| Saccharin | ♦500 | 30 | 76.20 | 85 | 1.11 | 0 |

*the doses in ppm refer to the quantity of Equivalent Metal.
♦the doses in ppm refer to the quantity of Active Ingredient.

Undesired effects refer to the appearance of necrosis or leaf decolouring.

TABLE 3

7-day preventive activity on *Plasmopara viticola* of blends of the copper (II) salt of salicylic acid ($Cu^{2+}SA_2$), which at 64 ppm*(g · x) is 85 (x).

| Blends | Doses ppm* (g · y) | Activity (y) | Blend activity according to Limpel (E) | Experimental blend activity | Synergy Factor | Undesired effects |
|---|---|---|---|---|---|---|
| **$TiO_2$ | 24 | 24 | 88.60 | 100 | 1.13 | 2 |
| Prussian blue | 12.5 | 13 | 86.95 | 100 | 1.15 | 4 |
| $FeSO_4$ | 28 | 40 | 91.00 | 100 | 1.09 | 5 |
| $ZnSO_4$ | 33 | 22 | 88.30 | 100 | 1.13 | 5 |

TABLE 3-continued 7-day preventive activity on *Plasmopara viticola* of blends of the copper (II) salt of salicylic acid ($Cu^{2+}SA_2$), which at 64 ppm*(g · x) is 85 (x).

| Blends | Doses ppm* (g · y) | Activity (y) | Blend activity according to Limpel (E) | Experimental blend activity | Synergy Factor | Undesired effects |
|---|---|---|---|---|---|---|
| $CuSO_4$ | 32 | 48 | 92.20 | 100 | 1.08 | 5 |
| **ZnO | 33 | 30 | 89.5 | 100 | 1.11 | 3 |

*the doses in ppm refer to the quantity of Equivalent Metal.
**$TiO_2$ has a particle size equal to 0.15 micron; ZnO has a particle size ranging of from 0.05 to 0.07 micron.

Undesired effects refer to the appearance of necrosis or leaf decolouring.

TABLE 4

7-day preventive activity on *Plasmopara viticola* of ternary blends:

| Blends | Dose ppm | Blend experimental activity | Undesired effects |
|---|---|---|---|
| $Cu^{2+} ASA_2$ + **$TiO_2$ + Prussian blue | 50 + 30 + 12.5 | 100 | 0 |
| $Cu^{2+} SA_2$ + **$TiO_2$ + Prussian blue | 50 + 30 + 12.5 | 100 | 0 |
| $Cu^{2+} SA$ + **$TiO_2$ + Prussian blue | 50 + 30 + 12.5 | 100 | 0 |

*the doses in ppm refer to the quantity of Equivalent Metal.
**$TiO_2$ has a particle size equal to 0.15 micron.

Undesired effects refer to the appearance of necrosis or leaf decolouring.

EXAMPLE 2

Efficacy of Blends of One or More Compounds Belonging to the Groups of Compounds ESA, PRO and MOD in the Control of *Peronospora Tabacina* on Tobacco in Preventive Leaf Application (Greenhouse Test)

Table 5

Leaves of cultivar Burley tobacco plants, grown in vases, in a conditioned environment (20±1° C., 70% relative humidity), were treated by spraying both sides of the leaves with the blends in question dispersed in an aqueous solution containing 0.3% of tween 20.

After remaining 7 days in a conditioned environment, the plants were infected on the lower side with an aqueous suspension of *Peronospora Tabacina* spores (200,000 spores per $cm^3$).

After remaining 24 hours in a humidity saturated environment, at 21° C., the plants were transferred to another conditioned environment for the incubation period of the fungus and, at the end of this period (7 days), the fungicidal activity is evaluated according to an evaluation percentage scale from 100 (healthy plant) to 0 (completely infected plant).

TABLE 5

7-day preventive activity on *Peronospora tabacina* of blends of the copper (II) salt of acetylsalicylic acid ($Cu^{2+} ASA_2$), which at 75 ppm*(g · x) is 85 (x).

| Blends | Doses ppm* (g · y) | Activity (y) | Blend activity according to Limpel (E) | Experimental blend activity | Synergy Factor | Undesired effects |
|---|---|---|---|---|---|---|
| **$TiO_2$ | 24 | 5 | 85.75 | 98 | 1.14 | 0 |
| $FeSO_4$ | 28 | 15 | 87.25 | 98 | 1.12 | 0 |
| $ZnSO_4$ | 33 | 20 | 88.0 | 98 | 1.14 | 0 |
| $CuSO_4$ | 32 | 45 | 91.75 | 100 | 1.09 | 0 |
| **ZnO | 33 | 15 | 87.25 | 97 | 1.11 | 0 |

*the doses in ppm refer to the quantity of Equivalent Metal.
**$TiO_2$ has a particle size equal to 0.15 micron; ZnO has a particle size ranging of from 0.05 to 0.07 micron.

Undesired effects refer to the appearance of necrosis or leaf decolouring.

EXAMPLE 3

Evaluation of the Phyto-Toxicity of Blends of One or More Compounds Belonging to the Groups of Compounds ESA, PRO and MOD on a Bean Plant in Preventive Leaf Application (Greenhouse Test)

Table 6

Leaves of cultivar Borlotto of Vigevano bean plants, grown in vases, in a conditioned environment (25±1° C., 60% relative humidity), were treated by spraying both sides of the leaves with the blends in question dispersed in an aqueous solution containing 0.3% of tween 20.

After 7 days in a conditioned environment, the intensity of the necrosis or leaf decolouring is evaluated with an evaluation scale from 100 (healthy plant) to 0 (plant completely infected with necrosis or decoloured).

TABLE 6

| Blends | Dose ppm | Leaf necrosis | Leaf decolouring |
|---|---|---|---|
| BTH | 125 | 10 | 40 |
| BTH + ATCA | 125 + 125 | 5 | 0 |
| BTH + TCA | 125 + 125 | 5 | 0 |
| BTH + cysteine | 125 + 125 | 8 | 2 |
| BTH + betaine | 125 + 125 | 2 | 0 |
| $Cu^{2+}ASA_2$ | 125 | 40 | 0 |
| $Cu^{2+}ASA_2$ + TCA | 125 + 125 | 0 | 0 |
| $Cu^{2+}ASA_2$ + ATCA | 125 + 125 | 0 | 0 |

TABLE 6-continued

| Blends | Dose ppm | Leaf necrosis | Leaf decolouring |
|---|---|---|---|
| $Cu^{2+}ASA_2$ + glutathione | 125 + 125 | 2 | 0 |
| $Cu^{2+}ASA_2$ + cysteine | 125 + 125 | 5 | 0 |
| $Cu^{2+}ASA_2$ + betaine | 125 + 125 | 2 | 0 |
| $Cu^{2+}$ SA | 125 | 55 | 5 |
| $Cu^{2+}$ SA + TCA | 125 + 125 | 5 | 0 |
| $Cu^{2+}$ SA + ATCA | 125 + 125 | 0 | 0 |
| $Cu^{2+}$ SA + glutathione | 125 + 125 | 5 | 0 |
| $Cu^{2+}$ SA + cysteine | 125 + 125 | 5 | 0 |
| $Cu^{2+}$ SA + betaine | 125 + 125 | 5 | 0 |
| INA | 125 | 50 | 10 |
| INA + TCA | 125 + 125 | 10 | 5 |
| INA + ATCA | 125 + 125 | 0 | 0 |
| INA + glutathione | 125 + 125 | 3 | 0 |
| INA + cysteine | 125 + 125 | 4 | 0 |
| BABA | 125 | 30 | 15 |
| BABA + TCA | 125 + 125 | 2 | 0 |
| BABA + ATCA | 125 + 125 | 0 | 0 |
| BABA + glutathione | 125 + 125 | 3 | 0 |
| BABA + cysteine | 125 + 125 | 2 | 0 |
| $Cu^{2+}$ $SA_2$ | 125 | 42 | 5 |
| $Cu^{2+}$ $SA_2$ + TCA | 125 + 125 | 3 | 0 |
| $Cu^{2+}$ $SA_2$ + ATCA | 125 + 125 | 0 | 0 |
| $Cu^{2+}$ $SA_2$ + glutathione | 125 + 125 | 2 | 0 |
| $Cu^{2+}$ $SA_2$ + cysteine | 125 + 125 | 2 | 0 |
| $Cu^{2+}$ $SA_2$ + betaine | 125 + 125 | 5 | 0 |

EXAMPLE 4

Efficacy of Blends of One or More Compounds Belonging to the Groups of Compounds ESA, PRO and MOD in the Control of *Plasmopara viticola* on Vines in Preventive Leaf Application (Greenhouse Test), with Elimination of Undesired Phyto-Toxicity Effects Table 7

TABLE 7

7-day preventive activity on *Plasmopara viticola* of blends of the copper (II) salt of salicylic acid ($Cu^{2+}SA_2$), which at 64 ppm*(g · x) is 85 (x). (The data without the addition of a MOD compound are already indicated in Table 3).

| Blends | Doses ppm* (g · y) | Activity (y) | Blend activity according to Limpel (E) | Experimental blend activity | Synergy Factor | Undesired effects |
|---|---|---|---|---|---|---|
| $TiO_2$ + ATCA* | 24 | 24 | 88.60 | 100 | 1.13 | 0 |
| Prussian blue + ATCA | 12.5 | 13 | 86.95 | 100 | 1.15 | 0 |
| $FeSO_4$ + TCA*** | 28 | 40 | 91.00 | 100 | 1.09 | 0 |
| $ZnSO_4$ + ATCA | 33 | 22 | 88.30 | 100 | 1.13 | 0 |
| $CuSO_4$ + TCA | 32 | 48 | 92.20 | 100 | 1.08 | 0 |
| **ZnO + ATCA | 33 | 30 | 89.5 | 100 | 1.11 | 0 |

*the doses in ppm refer to the quantity of Equivalent Metal.
**$TiO_2$ has a particle size equal to 0.15 micron; ZnO has a particle size ranging of from 0.05 to 0.07 micron;
***the dose of ATCA and TCA applied is 125 ppm. Undesired effects refer to the appearance of necrosis or leaf decolouring.

The invention claimed is:

1. A method for stimulating the natural defense systems of plants and inducing resistance in agricultural plants to phytopathogenic fungi comprising applying to said agricultural plants a mixture comprising two or more compounds where at least one compound is selected from i) and one compound is selected from ii):

i) at least a salicylic acid derivative of formula (I):

$$\begin{array}{c} X \diagdown \diagup Y-R_1 \\ \diagdown \diagup \\ \diagup \diagdown O-R_2 \\ (R_3)_n \end{array} \quad (I)$$

wherein:
$R_1$ represents a copper$^{+2}$ cation;
$R_2$ represents a hydrogen atom or an COR' acyl group;
R' represents a hydrogen atom, a $C_1$-$C_6$ alkyl group, or a phenyl group;
n is a number between 0 and 2;
$R_3$ is the same or different when n is 2 and $R_3$ represents fluorine, chlorine, bromine or iodine; a $C_1$-$C_6$ alkyl group, a $C_1$-$C_6$ alkoxyl group, a $C_1$-$C_6$ thioalkyl group, a $C_2$-$C_7$ carbo-alkoxyl group, or a cyano group;
X and Y are the same or different and are oxygen; and
ii) titanium dioxide.

2. The method according to claim 1, wherein the application of the mixture is effected on the leaves, stems, branches and roots, or on the seeds before sowing, or on the ground in which the plant grows.

3. The method according to claim 1, characterized in that the quantity of each compound selected from i) and ii) that is applied, is applied in a quantity ranging from 0.5 g to 5 kg per hectare.

4. The method according to claim 1, characterized in that the acid/copper$^{+2}$ molar ratio is 1:1 or 2:1 for the copper$^{+2}$.

5. The method according to claim 1, characterized in that the titanium dioxide is in micronized form.

6. The method according to claim 5, characterized in that the micronized form of titanium dioxide have a particle size lower than 1 micron.

7. The method according to claim 1, where the mixture comprising two or more compounds comprises other active principles selected from other fungicides, phytoregulators, antibiotics, herbicides, insecticides, and fertilizers compatible with the titanium dioxide.

8. A method as defined in claim 1 wherein the salicylic acid derivative is acetylsalicylic acid.

9. A method as defined in claim 1 wherein the salicylic acid derivative is salicyclic acid.

* * * * *